US006702576B2

(12) United States Patent
Fischer et al.

(10) Patent No.: US 6,702,576 B2
(45) Date of Patent: Mar. 9, 2004

(54) LIGHT-CURING DEVICE WITH DETACHABLY INTERCONNECTING LIGHT APPLICATOR

(75) Inventors: Dan E. Fischer, Sandy, UT (US); Bruce S. McLean, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 10/080,489

(22) Filed: Feb. 22, 2002

(65) Prior Publication Data

US 2003/0162143 A1 Aug. 28, 2003

(51) Int. Cl.7 .................................................. A61C 3/00

(52) U.S. Cl. ...................................................... 433/29

(58) Field of Search ....................... 433/29; 250/504 H

(56) References Cited

U.S. PATENT DOCUMENTS

| 4,281,366 A | | 7/1981 | Wurster et al. |
| 4,309,617 A | * | 1/1982 | Long ........................ 250/504 H |
| 4,348,180 A | | 9/1982 | Schuss ........................ 433/126 |
| 4,666,405 A | * | 5/1987 | Ericson ....................... 433/229 |
| 4,666,406 A | | 5/1987 | Kanca, III |
| 4,963,798 A | | 10/1990 | McDermott |
| 5,115,761 A | | 5/1992 | Hood |
| 5,123,845 A | | 6/1992 | Vassiliadis et al. |
| 5,139,495 A | | 8/1992 | Daikuzono |
| 5,161,879 A | | 11/1992 | McDermott |
| 5,275,564 A | | 1/1994 | Vassiliadis et al. |
| 5,328,368 A | | 7/1994 | Lansing et al. |
| 5,348,552 A | | 9/1994 | Nakajima et al. |
| 5,415,543 A | | 5/1995 | Rozmajzl, Jr. |
| 5,420,768 A | | 5/1995 | Kennedy |
| D361,382 S | | 8/1995 | Brunsell et al. |
| 5,457,611 A | | 10/1995 | Verderber |
| 5,616,141 A | | 4/1997 | Cipolla |
| 5,634,711 A | | 6/1997 | Kennedy et al. |
| D385,051 S | | 10/1997 | Wu |
| D385,630 S | | 10/1997 | Lieb et al. |
| 5,772,643 A | | 6/1998 | Howell et al. ............... 604/283 |
| 5,797,740 A | | 8/1998 | Lundvik |
| 5,803,729 A | | 9/1998 | Tsimerman |
| 5,908,294 A | | 6/1999 | Schick et al. |
| 5,908,295 A | | 6/1999 | Kawata |
| 5,912,470 A | | 6/1999 | Eibofner et al. |

(List continued on next page.)

FOREIGN PATENT DOCUMENTS

WO         WO 99/35995         7/1999

OTHER PUBLICATIONS

*3M Curing Light XL3000 (Project 95–23, Section 2b of DIS #47* (Jan. 23, 2002).
"Acta Curing Light" www.amadent.com (Jan. 23, 2002).
"All–Cure", www.all–cure.com (Jan. 23, 2002).
"ARC Light IIM", Air Techniques Inc.

(List continued on next page.)

*Primary Examiner*—John J. Wilson
(74) *Attorney, Agent, or Firm*—Workman Nydegger

(57) ABSTRACT

The light-curing devices of the invention include a gripping member configured to be held in the hand of a user, a light applicator configured in size and shape to be inserted within the mouth of a user, and a light source configured to generate and emit sufficient radiant energy for curing light-sensitive compounds. The light-curing devices also include connection means configured for detachably connecting the light applicator and the gripping member in such a manner as to prevent the light applicator from rotating with respect to the gripping member. The light applicator may include a light guide or a light source and corresponding mounting structure. The connection means may include mating bayonet formations, tongue and groove type formations, internesting pin and pinhole formations, latches and other interconnecting structures.

25 Claims, 5 Drawing Sheets

U.S. PATENT DOCUMENTS

| | | | |
|---|---|---|---|
| 5,921,777 A | | 7/1999 | Dorman ................. 433/126 |
| 6,033,223 A | * | 3/2000 | Narusawa et al. ......... 433/226 |
| 6,077,073 A | | 6/2000 | Jacob ................. 433/29 |
| 6,095,812 A | | 8/2000 | Senn et al. |
| 6,102,696 A | | 8/2000 | Osterwalder et al. |
| 6,208,788 B1 | * | 3/2001 | Nosov ................. 433/29 |
| 6,318,996 B1 | | 11/2001 | Melikechi et al. |
| 6,322,358 B1 | | 11/2001 | Senn et al. |
| 6,325,623 B1 | | 12/2001 | Melnyk et al. |
| 6,331,111 B1 | | 12/2001 | Cao |
| 6,419,483 B1 | * | 7/2002 | Adam et al. ............. 433/29 |
| 6,468,077 B1 | | 10/2002 | Melikechi et al. ......... 433/29 |
| 6,482,004 B1 | | 11/2002 | Senn et al. ............. 433/29 |
| 6,511,317 B2 | | 1/2003 | Melikechi et al. ......... 433/29 |
| 2001/0038992 A1 | | 11/2001 | Otsuka ................. 433/29 |
| 2001/0046652 A1 | | 11/2001 | Ostler et al. ............. 433/29 |
| 2001/0093833 | | 7/2002 | West ................. 362/555 |
| 2002/0115037 A1 | | 8/2002 | Cao ................. 433/29 |
| 2001/0133970 | | 9/2002 | Gordon et al. ............. 34/250 |
| 2002/0163317 A1 | | 11/2002 | Cao ................. 315/291 |
| 2002/0167283 A1 | | 11/2002 | Cao ................. 315/291 |
| 2002/0168603 A1 | | 11/2002 | Cao ................. 433/29 |
| 2002/0168604 A1 | | 11/2002 | Cao ................. 433/29 |
| 2002/0168605 A1 | | 11/2002 | Cao ................. 433/29 |
| 2002/0168606 A1 | | 11/2002 | Cao ................. 433/29 |
| 2002/0168607 A1 | | 11/2002 | Cao ................. 433/29 |
| 2002/0168608 A1 | | 11/2002 | Cao ................. 433/29 |
| 2002/0172912 A1 | | 11/2002 | Cao ................. 433/29 |
| 2002/0172913 A1 | | 11/2002 | Cao ................. 433/29 |
| 2002/0172914 A1 | | 11/2002 | Cao ................. 433/29 |
| 2002/0172915 A1 | | 11/2002 | Cao ................. 433/29 |
| 2002/0172916 A1 | | 11/2002 | Cao ................. 433/29 |
| 2002/0172917 A1 | | 11/2002 | Cao ................. 433/29 |
| 2002/0175352 A1 | | 11/2002 | Cao ................. 257/258 |
| 2002/0175628 A1 | | 11/2002 | Cao ................. 315/56 |
| 2002/0177095 A1 | | 11/2002 | Cao ................. 433/29 |
| 2002/0177096 A1 | | 11/2002 | Cao ................. 433/29 |
| 2002/0177099 A1 | | 11/2002 | Cao ................. 433/29 |
| 2002/0180368 A1 | | 12/2002 | Cao ................. 315/149 |
| 2002/0181947 A1 | | 12/2002 | Cao ................. 392/409 |
| 2002/0182561 A1 | | 12/2002 | Cao ................. 433/29 |
| 2002/0182562 A1 | | 12/2002 | Cao ................. 433/29 |
| 2002/0190659 A1 | | 12/2002 | Cao ................. 315/149 |
| 2002/0190660 A1 | | 12/2002 | Cao ................. 315/149 |
| 2002/0197582 A1 | | 12/2002 | Cao ................. 433/29 |
| 2003/0001507 A1 | | 1/2003 | Cao ................. 315/56 |
| 2003/0038291 A1 | | 2/2003 | Cao ................. 257/81 |
| 2003/0039119 A1 | | 2/2003 | Cao ................. 362/227 |
| 2003/0039120 A1 | | 2/2003 | Cao ................. 362/227 |
| 2003/0039122 A1 | | 2/2003 | Cao ................. 362/294 |
| 2003/0040200 A1 | | 2/2003 | Cao ................. 438/800 |

OTHER PUBLICATIONS

"Bellini X Ray", www.bellinixray.com (Jan. 23, 2002).
"DENTAMERICA–Litex", www.dentamerica.com (Jan. 23, 2002).
"Elipar FreeLight Curing Light", 3M ESPE, cms.3m.com (Jan. 23, 2002).
"Elipar Highlight Curing Light (Project 97–22)", ESPE America, Inc. (Jan. 23, 2002).
"Excelite", TOESCO.
"Hilux 350 Curing Light (Project 97–34)", First Medica, Inc. (Jan. 23, 2002).
"Just Cure It", Air Techniques, Inc. (Jan. 25, 2002).
*Luna 8*™, www.luma–lite.com (Jan. 30, 2001).
*LumaCure Cordless Curing Light (Project 1–16), Product Evaluations DIS 64* (Jan. 23, 2002).
"LUXoMAX the Latest News from Akeda Dental", Akeda Dental A/S, www.akeda.dk (Oct. 1, 2001).
"NRG L.E.D. Curing Light", Denstply Caulk (2001).
"Optilux 500 Polymerization Unit (Project 96–33)", Demetron Research Corporation/Kerr (Jan. 23, 2002).
"Optilux 501 Polymerization Unit (Project 00–03)", Kerr/Demetron (Jan. 23, 2002).
"RemeCre CL15", Remedent, www.remedent.com (Jan. 23, 2002).
"Resin Curing Lights" Clinical Research Associates Newsletter, (Mar. 1996).
"Resin Curing Lights: What You Should Know", Contemporary Esthetics and Restorative Practice, p. 36 (Nov. 2001).
"Savings on Curing Lights from Lone Star Dental Corp.", Lone Star Dental Corp., www.dentequip.com (Jan. 23, 2002).
"Starlight" Mectron Medical Technology.
"The Power PAC", American Dental Technologies, www.americandentaltech.com (Jan. 23, 2002).
"Variable Intensity Polymerizer Light curing Unit (VIP) (Project 99–14)", BISCO, Inc. (Jan. 23, 2002).
"VivaluxII Cordless Polymerization Unit (Project 96–39)", Ivoclar North America (Jan. 23, 2002).
"ZAP Dual Curing Light (Project 1–26)", CSM–Dental (Denmark)/Soft–core Texas, Inc., (Jan. 23, 2002).

* cited by examiner

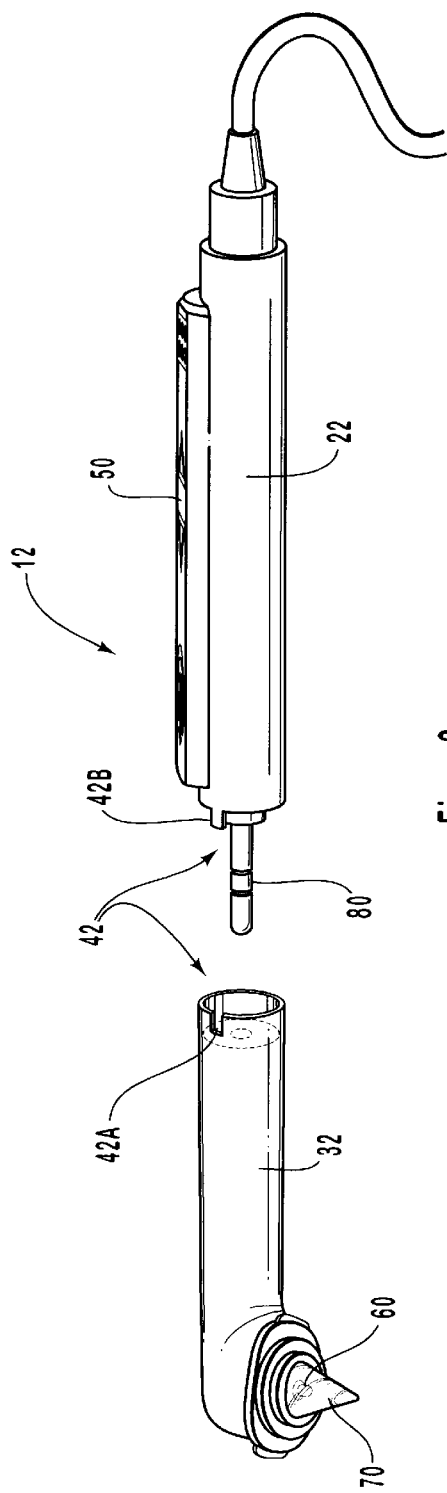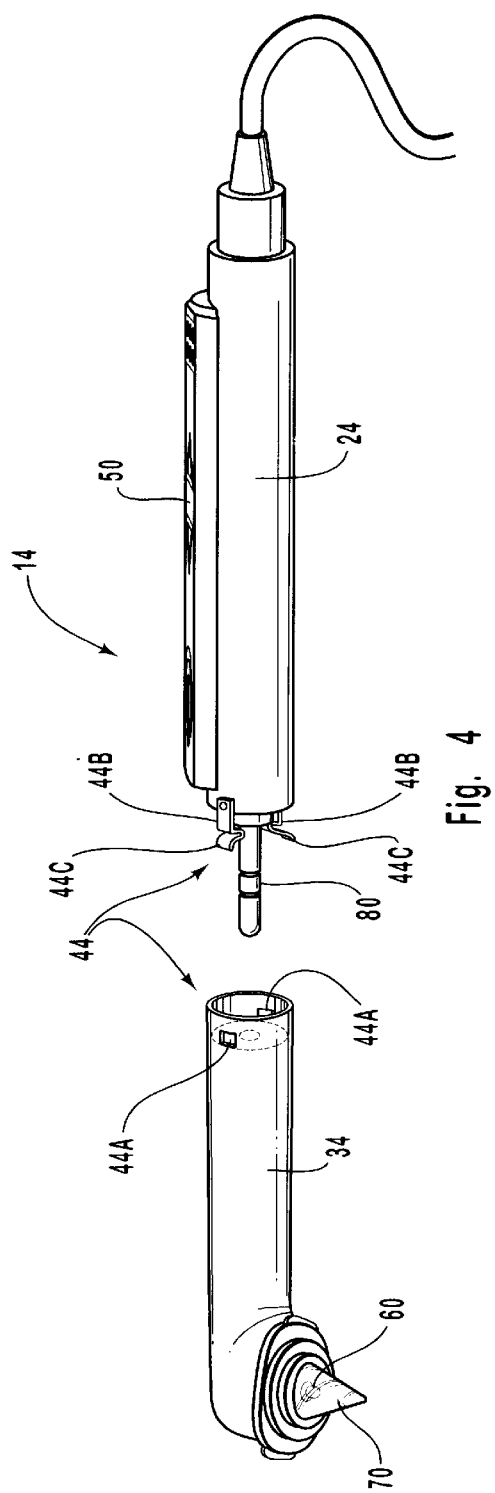

LIGHT-CURING DEVICE WITH DETACHABLY INTERCONNECTING LIGHT APPLICATOR

BACKGROUND OF THE INVENTION

1. The Field of the Invention

The present invention is in the field of light-curing devices and, more particularly, in the field of dental light-curing devices configured for curing light-curable compounds.

2. The Relevant Technology

Light-curing device are commonly used in the dental industry to irradiate and cure light-sensitive compounds. Many of the existing light-curing devices include internal light sources, such as halogen lamps or light emitting diodes, which are configured for generating and emitting light that is suitable for curing the light-sensitive compounds. Because many existing light-curing devices are to large to fit within a patient's mouth, particularly gun-shaped devices, the light-curing devices are typically coupled with a detachable light guide which is configured to capture and channel the light through optical fiber, or other mediums, to a desire application site within the patient's mouth, such as, for example, a dental restoration. In some dental procedures, the light guide can be equipped with an attachment, which can be used to directly manipulate and compress the photosensitive compounds while the light is applied to the site. This contact with the light guide is useful because it generally enables the practitioner to ensure the dental compound is properly applied within the dental restoration.

One problem with using the light guide in this manner, however, is that existing light curing devices and light guides are not configured to interconnect in such a manner as to prevent the rotation and swiveling of the light guide, which may occur as a result of applying pushing and pulling forces with the light-curing device, particularly when the light guide or other light applicator is curved. Existing light guides are typically configured with a recess that circumferentially extends around the base of the light guide and which is configured for receiving a retaining ring disposed within the end of the light-curing device. Although the retaining ring is configured to internest within the recess of the light guide, it is not configured to prevent rotation of the light guide about the end of the light-curing device. Consequently, the light guide is susceptible to rotating during use, particularly when irregular forces are applied during the dental procedure, as generally described above. Rotation of the light guide is undesirable because it minimizes the control that can be exercised by the practitioner in manipulating the dental compound with the light guide. Rotation of the light guide can also potentially cause damage to sensitive mouth and dental tissues as a result of rotating unpredictably within the patient's mouth.

Other light-curing devices, having light sources disposed directly at the distal end of the light-curing device, do not require a light guide to capture and transmit the light to the desired application site. Instead, these integrated light-curing devices are configured with a narrow body with a distally located light source that can be inserted directly into the patient's mouth. These light-curing devices are useful for at least minimizing the risks associated with uncontrolled rotation. Existing integrated light-curing devices have no moving parts and are therefore very suitable for enabling a practitioner to compress and otherwise manipulate the dental compound during the dental procedure, such as with a transparent attachment placed over the light source at the tip of the light-curing device.

One problem with the integrated light-curing devices, however, is that inasmuch as they are integrally connected, the light sources or light applicators located at the end of the light-curing device, which are inserted into the patient's mouth, cannot be interchanged. It is desirable to interchange the light applicator, which includes the portion of the light-curing device that is inserted into the patient's mouth, between uses to preserve the sanitation of the light-curing device. For instance, is useful to interchange the light applicator when it becomes contaminated, damaged, or otherwise unusable.

Accordingly, in view of the foregoing, there is currently a need in the art for improved light curing device configured to reduce uncontrolled rotation of the light applicator within the patient's mouth.

SUMMARY OF PRESENTLY PREFERRED EMBODIMENTS

Briefly summarized, presently preferred embodiments of the present invention are directed to improved light-curing devices configured so as to prevent significant rotation of the light applicator within the patient's mouth.

According to one presently preferred embodiment, the light-curing device includes a body having a gripping member, a detachably interconnecting light applicator, and a light source. The light source is configured to generate and emit light that is suitable for irradiating and curing light-curable compounds. In one embodiment, the light source is contained at least partially within the light applicator, which is configured in size and shape to be inserted at least partially within a patient's mouth during use. In another embodiment, the light source is contained at least partially within the gripping member, which is configured for being held within the hand of a dental practitioner, in which case the light applicator includes a light guide. The light applicator may also include lenses, special shields, tips, and other transparent attachments, which may be integrally connected to or detachably connected with the light applicator and which are configured for compressing and otherwise manipulating the light-curable compound during irradiation and curing of the light-curable compound.

The light-curing devices of the invention also include connection means for connecting the light applicator and the gripping member in such a manner as to reduce significant rotation of the light applicator with respect to the gripping member, particularly during manipulation of the light-curable compound. In one embodiment, the connection means includes the components of a bayonet type connection disposed in the light applicator and the gripping member. Connection means may also include the components of tongue and groove type connections, internesting pin and pinhole connections, latches, clips and any other interconnecting structure configured to prevent significant rotation of the light applicator with respect to the gripping member.

It will be appreciated that the light-curing devices of the invention are useful for at least enabling a practitioner to use the light applicators of the light-curing devices as tools for compressing and manipulating the dental compounds during dental restoration procedures without enabling the light applicator to rotate with respect to the gripping member, as otherwise occurs with certain existing light-curing devices. The light-curing devices of the invention also enable the associated light applicators to be controllably detached from the gripping members for enabling the light applicators to be interchanged or replaced when desired.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 3 illustrates a perspective view of one embodiment of the light-curing device in which the connection means comprises the components of a tongue and groove connection;

FIG. 4 illustrates a perspective view of one embodiment of the light-curing device in which the connection means comprises the components of a latching connection;

DETAILED DESCRIPTION OF THE PREFERRED EMBODIMENTS

Figure 1:
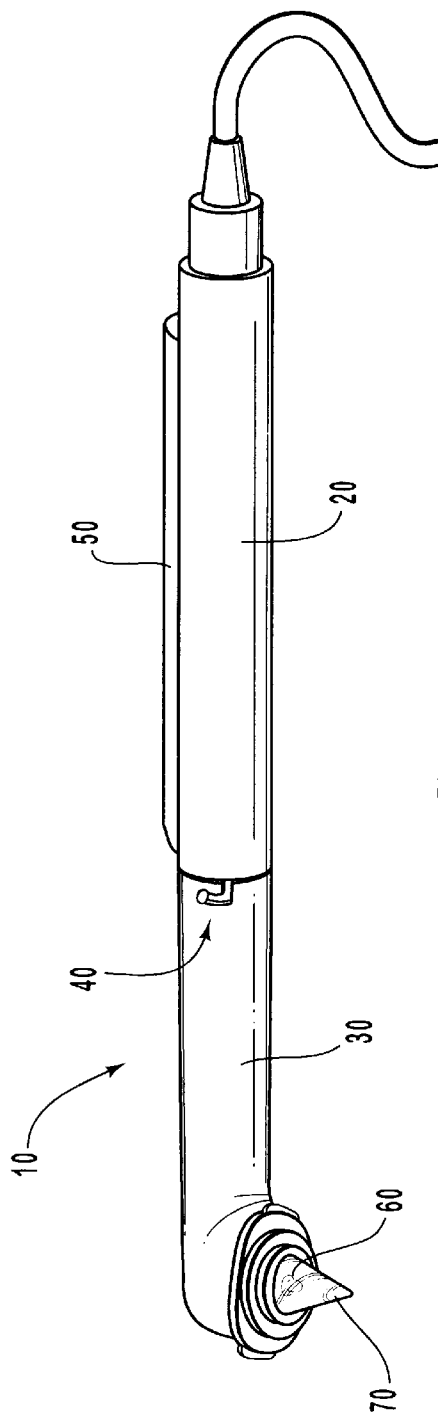
FIG. 1 illustrates a perspective view of one presently preferred embodiment of the light-curing device of the invention that includes a gripping member, a light applicator with a light source and a transparent attachment, and connection means comprising a bayonet connection.

A detailed description of the light-curing device of the invention will now be provided with specific reference to figures illustrating preferred embodiments of the invention. It will be appreciated that like structures will be provided with like reference designations. To provide context for interpreting the scope of the invention, certain terms used throughout the application will now be defined.

The term "light applicator," as used herein, refers to a portion of the light-curing device that is configured in size and shape to be inserted at least partially within the mouth of a patient and which is also configured to transmit, emit, direct, or otherwise apply light to a desired application site within the patient's mouth. By way of example, and not limitation, the light applicator includes, in one embodiment, a standard light guide configured to be attached to a light-curing device for channeling and directing light emitted from a remotely located light source. The light applicator includes, in another embodiment, a light source and corresponding mounting structures configured in size and shape to be inserted into a patient's mouth. The light applicator may also include integral and detachable shields, lenses, and other transparent attachments which are configured to be inserted within the patient's mouth.

The term "transparent attachment" and "transparent tip," which are used interchangeably herein, refer to structure that is configured for manipulation of a light-curable compound and includes at least a transparent tip through which light passes during the light-curing procedure. According to one embodiment, the transparent attachment may be color tinted or treated for creating a desired effect, such as, but not limited to, filtering undesired frequencies of light. The transparent attachment may also include optical focusing, collimating, or dispersing attributes for directing the light to the desired application site in a desired manner.

The term "gripping member," as defined herein, refers to a portion of the light-curing device that is specifically configured for being held in the hand of a dental practitioner performing a dental procedure under normal conditions.

The term "light source" includes any light generating device, including, but not limited to, a halogen bulb, a light-emitting diode (LEDs), an LED array, and combinations thereof.

The term "manipulate," is defined herein to include the act of moving, compressing, working, pulling, pushing and otherwise contacting. Although the term manipulate is sometimes used herein with specific reference to moving, compressing, working, pulling, pushing or contacting light-curable compounds with the transparent attachments during dental procedures, it will be appreciated that the transparent attachments described herein may also be used to manipulate matrix bands and other objects and compounds used during dental procedures and other procedures requiring the use of a light-curing device.

The terms "light-sensitive compound," "light-curable compound," and "compound" are used interchangeably herein and refer to compounds that are configured to solidify or otherwise cure upon receiving appropriate radiant energy in the form of light from a light source of a light-curing device.

In general, the light-curing devices of the invention, as described herein, are configured with connection means for detachably connecting the gripping member and the light applicator in a manner that prevents significant rotation of the light applicator and while enabling the light applicator to be controllably detached from the gripping member. It will be appreciated that these are improvements over the existing devices in the art.

The term "significant rotation," as used herein, is defined as angular rotation of the light applicator relative to the gripping member that is at least 10°.

FIG. 1 illustrates one presently preferred embodiment of the light-curing device of the invention. As shown, the light-curing device 10 includes a gripping member 20 that is interconnected with a light applicator 30 by connection means 40, each of which will now be described. The gripping member 20 is preferably configured in size and shape for being held in the hand of a user, such as a dental practitioner. The gripping member 20, according to one embodiment, includes a control panel 50 for enabling the user to control the operation of the light-curing device with finger manipulation. The control panel 50 may be configured to provide any desired functionality. For instance, by way of example and not limitation, the control panel 50 may enable the user to increase and decrease the duration of time in which the light-curing device 10 is activated and for activating and deactivating the light-curing device 10.

During use, the light-curing device 10 is activated and a light source 60 disposed at the end of the light applicator 10 is illuminated, thereby generating light that is suitable for irradiating and curing light-sensitive compounds. The light source may include any quantity of LEDs and LED arrays.

As shown, the light applicator 30 is configured in shape and size for being inserted at least partially into the mouth of a patient, during use, for directing the light emitted from the light source to a desired site within the patient's mouth. During dental procedures, such as dental restorations, a light-curable compound is applied to a tooth. It is sometimes desirable to manipulate the compound before and during irradiation of the compound with radiant energy suitable for curing the compound. For instance, it is sometimes desirable to compress the compound within the treated tooth to ensure air pockets have been removed from the dental restoration before the compound is completely cured and to obtain the desired restoration effect. To facilitate the manipulation of the compound during the dental procedure it has been found that an attachment, such as transparent attachment 70, can be connected to the light applicator 30 and used as a tool for manipulating the compound as desired. One non-limiting example of a suitable transparent attachment, includes a Denbur type attachment 72, such as the Denbur Lite-Tip®, shown in FIGS. 6 and 7 and which is well-known in the art. Transparent attachments 70 and 72 comprise two non-limiting examples of suitable structure configured for manipulation of a light-curable compound during a light-curing procedure with the light-curing devices of the invention.

In one embodiment, transparent attachment 70 integrally connected to the light applicator, such as with an adhesive welding, or mechanical coupling. The transparent attachment 70 can also be detachably connected with the light applicator 30 with a releasable mechanical coupling, such as a snap fit.

Although the transparent attachment 70 has been described as structure for manipulating the light-sensitive compound, it will be appreciated that the transparent attachment 70 may also be configured to provide a desired optical effect, such as filtering undesired frequencies of light, and refracting or otherwise redirecting the path of the light emitted from the light source 60. For instance, by way of example and not limitation, the transparent attachment 70 may include color-tinted lenses.

During use, in which the transparent attachment 70 is used to manipulate the light-sensitive compound, it is desirable to prevent significant rotation of the light applicator 30 with respect to the gripping member 20 to provide the user with optimum control over the manipulation of compound with the transparent attachment 70. It is also desirable to enable the light applicator to be interchanged and replaced between uses to at least maintain a desired level of sanitation. These desirable characteristics are provided by the light-curing devices of the present invention with the connection means 40. In particular, the connection means 40 is configured to detachably interconnect the gripping member 20 and the light applicator 30 in a manner that prevents significant rotation of the light applicator 30 with respect to the gripping member 20.

As shown in FIG. 1, the connection means 40 includes the components of a bayonet type connection which interconnect the light applicator 30 and the gripping member 20 in a manner configured for preventing the light applicator 30 from rotating or detaching during use in dental procedures. In particular, the connection means 40 includes a radial slot formation 40A configured to receivably engage a pin 40B. Once the pin 40B is appropriately inserted and radially disposed within the radial slot formation 40A, such that the pin 40B is disposed within the retaining portion 40C of the radial slot formation 40A, then the connection means 40 is effectively able to prevent significant rotation of the light applicator 30 with respect to the gripping member 20. It will be appreciated that this is useful, particularly when the transparent attachment 70 is used to manipulate the light-curable compounds during the dental procedure This embodiment is also particularly useful for preventing longitudinal displacement of the light applicator 30 with respect to the gripping member 20 such as, for example, when the pulling forces are applied on the gripping member 20 during the dental procedure, as generally described above.

Figure 2:
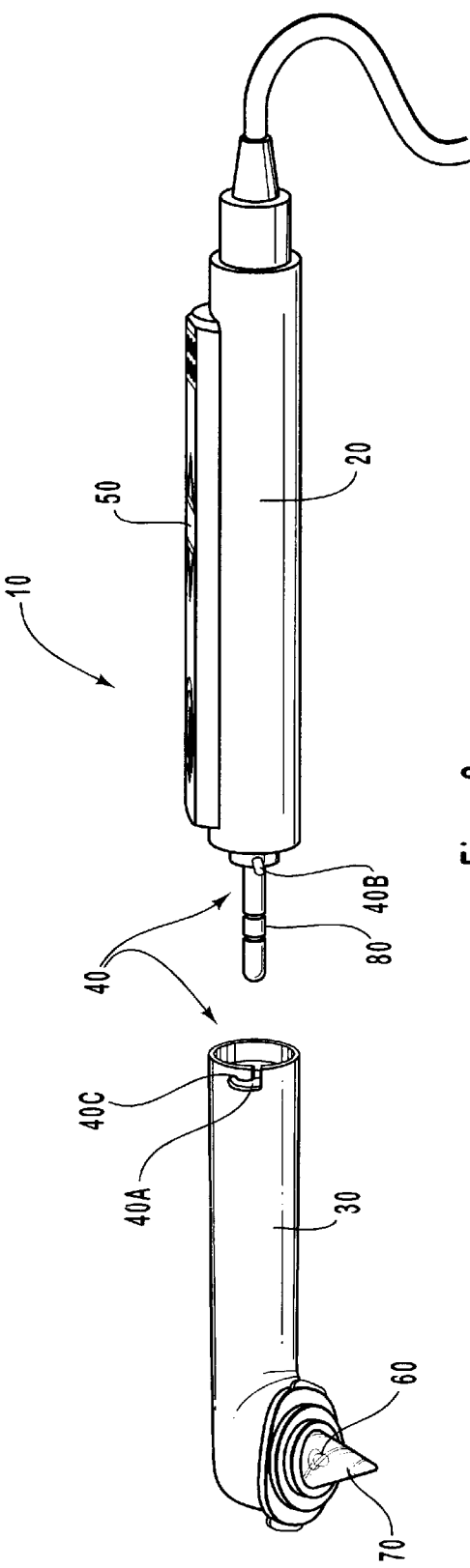
FIG. 2 illustrates a perspective view of the light-curing device illustrated in FIG. 1 in which the transparent attachment, the light applicator and the gripping member are separated.

As shown in FIG. 2, the connection means 40 also provides the functionality of enabling the light applicator 30 to be detached from the gripping member 20. It will be appreciated that the force required to connect the light applicator 30 and gripping member 20 may vary to accommodate different needs and preferences and to provide a desired connection for preventing significant rotation of the light applicator 30 with respect to the gripping member 20 while still enabling the light applicator 30 to be controllably detached from the gripping member 20.

FIG. 2 also illustrates an electrically conductive pin 80 configured to electrically couple the light applicator 30 and gripping member 20 for empowering the light source 44 during use. It will be appreciated, however, that the electrical coupling of the light applicator 30 and the gripping member 20 is not limited to any particular type of connection. For instance, the electrical coupling between the light applicator 30 and the gripping member 20 may also include electrically conductive surfaces, a plurality of conductive pins, or any other electrical coupling components.

According to another embodiment, not shown, the light applicator does not contain a light source. Instead, the light source is disposed in the gripping member or at a remote location, wherein the light is transmitted between the gripping member and the light applicator with an optical fiber or another light transmitting medium, and wherein the coupling between the gripping member and the light applicator comprises an optical interface.

FIG. 3 illustrates one embodiment of the light-curing device 12 of the invention in which the light applicator 32 and the gripping member 22 are configured to be detachably interconnected with connection means 42 comprising the components of a tongue and groove connection. In particular, the connection means 42 includes a recessed groove 42A configured to frictionally receive a protrusion 42B. When the protrusion 42B is inserted into the recessed groove 42A then the connection means 42 is effectively able to prevent the light applicator 32 from rotating with respect to the gripping member 22. In all other respects the light-curing device 12 is the same as the light-curing device disclosed in FIGS. 1 and 2.

FIG. 4 illustrates one embodiment of the light-curing device 14 of the invention in which the light applicator 34 and the gripping member 24 are configured to be detachably interconnected with connection means 44 comprising the components of a latching connection. In particular, the connection means 44 includes recesses 44A configured to receive and interconnect with a latches 44B. This embodiment is useful because the latches 44B are specifically configured to interconnect with the recesses 44A in such a manner as to prevent longitudinal separation of the light applicator 34 and the gripping member 24, during the dental procedure, in addition to preventing the aforementioned significant rotation of the light applicator 34. It will be appreciated that this is particularly useful when pulling forces are applied to the gripping member 24. In one embodiment, as shown, the latches 44B are also configured with lips 44C for providing means for pulling the latches 44B out from engagement with the recesses 44A, and for thereby enabling the light applicator 34 to be controllably detached from the gripping member 24 when desired. In all other respects the light-curing device 14 is the same as the light-curing device disclosed in FIGS. 1 and 2.

Figure 5:
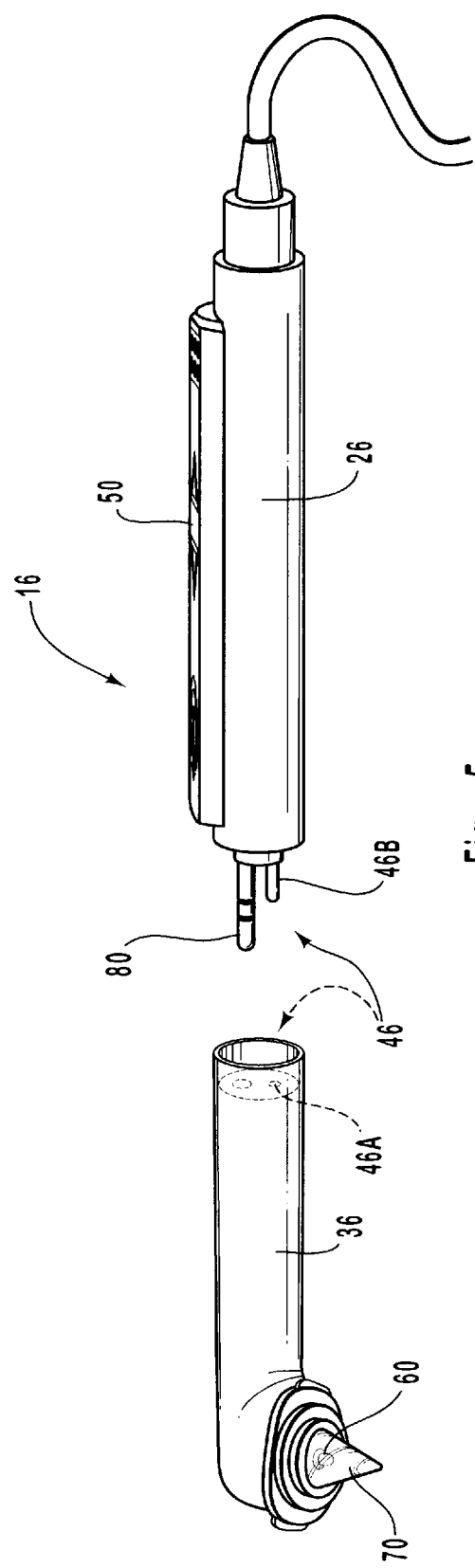
FIG. 5 illustrates a perspective view of one embodiment of the light-curing device in which the connection means comprises the components of a pin and pinhole connection.

FIG. 5 illustrates one embodiment of the light-curing device 16 of the invention in which the light applicator 36 and the gripping member 26 are configured to be detachably interconnected with connection means 46 comprising the components of a pin and pinhole connection. In particular, the connection means 46 includes a pinhole 46A configured to receivably engage a pin 46B. Once the pin 46B is completely inserted within the pinhole 46A then the connection means 46 is effectively able to prevent significant rotation of the light applicator 36 with respect to the gripping member 26. In all other respects the light-curing device 16 is the same as the light-curing device disclosed in FIGS. 1 and 2.

Although specific examples have been provided regarding the specific configurations of the connection means of the invention, it will be appreciated that the connection means can also include other combinations of interensting and interconnecting structure, as well as any combination of the components of the aforementioned connection means. Furthermore, it will also be appreciated that the light-curing devices of the invention are not limited to any particular size, shape or design and can, therefore, include other shapes, sizes and designs without departing from the scope of the present invention. For instance, although FIGS. 1–5 illustrate light applicators and gripping members designed with narrow and generally cylindrical bodies configured for being interconnected into substantially concentric alignment, it is not necessary that the light applicators or the gripping devices comprise narrow straight bodies or that they are concentrically aligned. For example, as shown in FIGS. 6 and 7, the light-curing device 18 may also include a light applicator 38 having a curved body and a gripping member 38 having the general shape of a gun.

Figure 6:
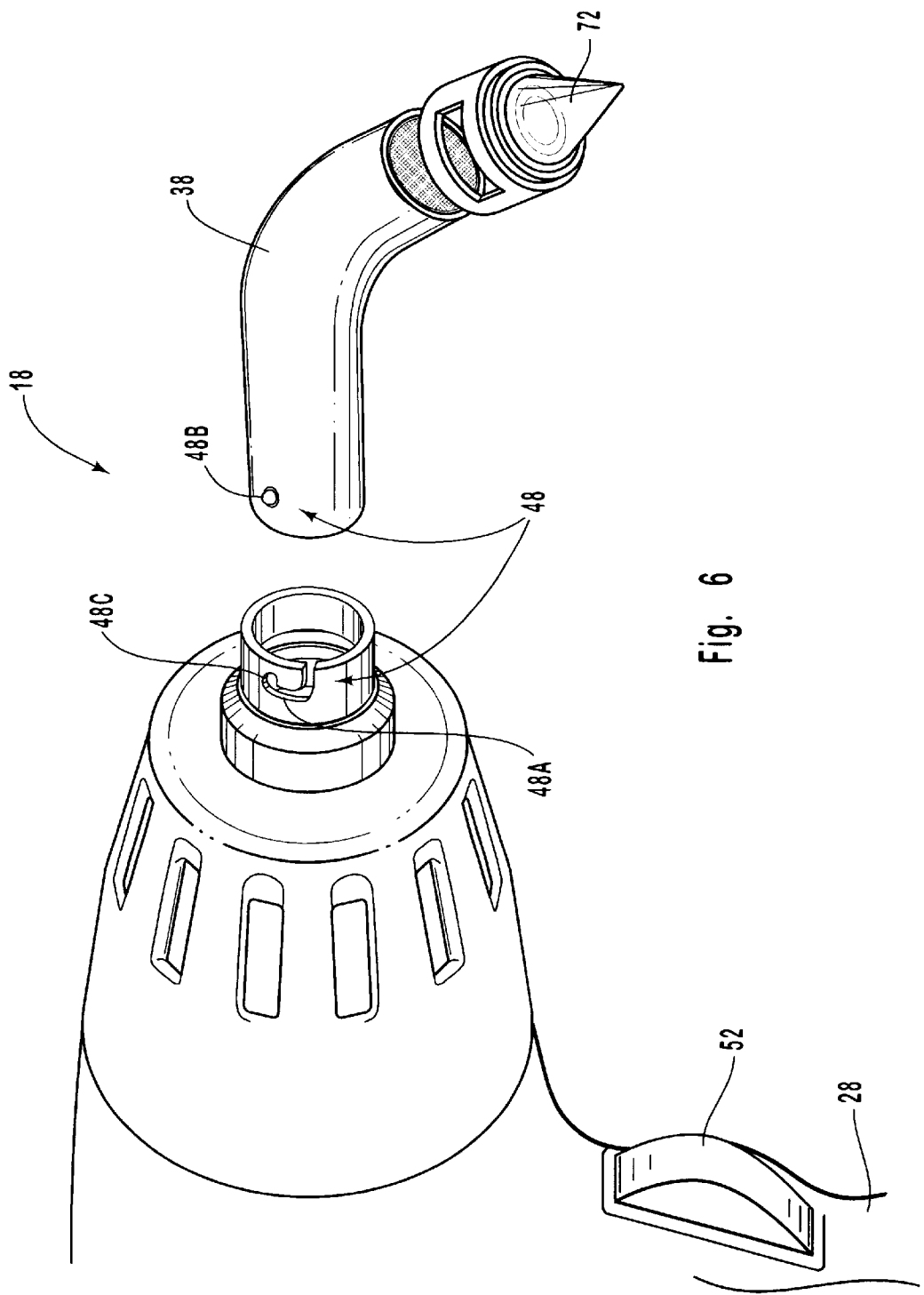
FIG. 6 illustrates a perspective view of one embodiment of the light-curing device of the invention in which a gripping member comprises the general shape of a gun, a light applicator comprising a light guide, an connection means comprising the components of a bayonet connection, and a transparent attachment are separated.
Figure 7:
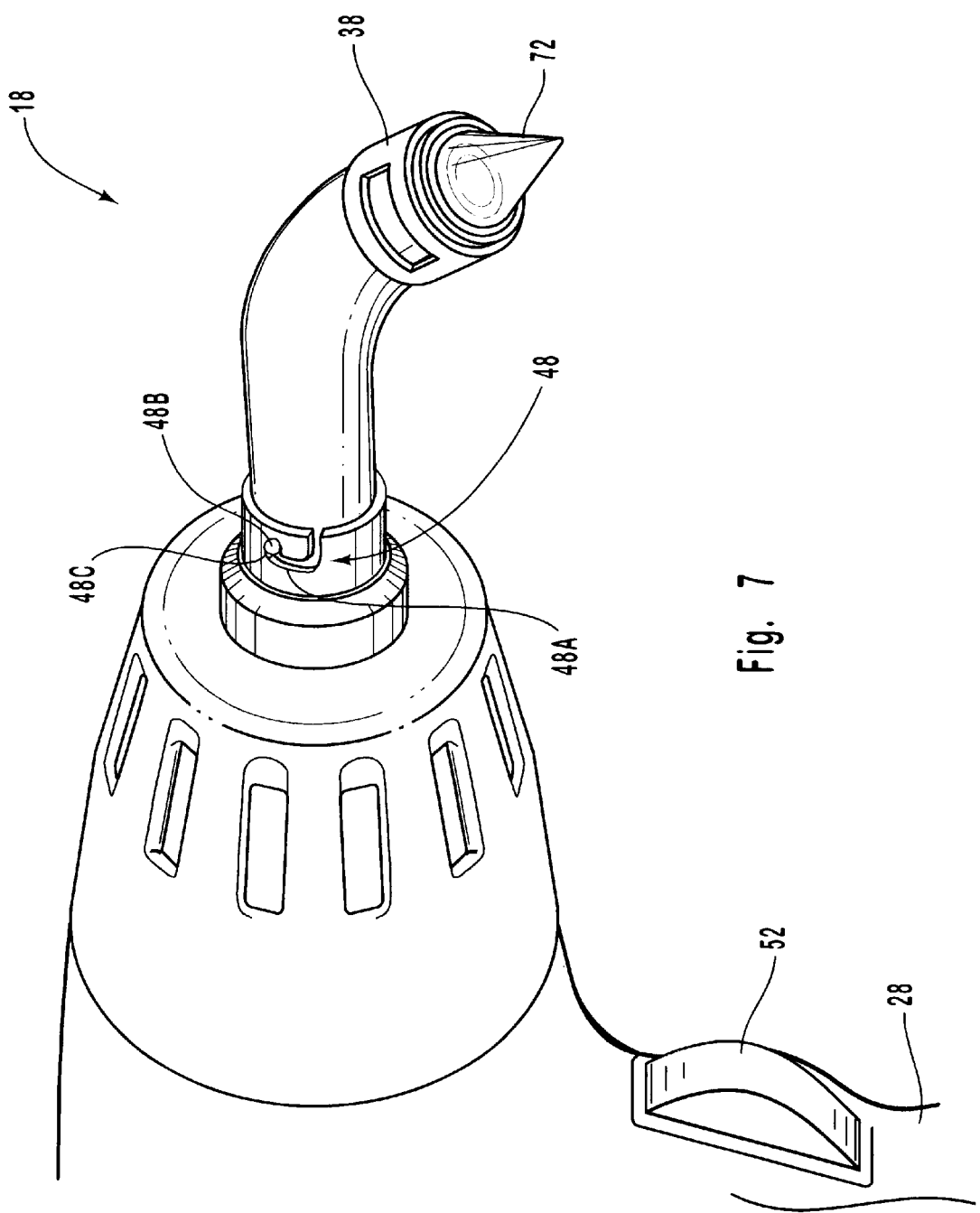
FIG. 7 illustrates a perspective view of one embodiment of the light-curing device of the invention that includes a gripping member comprising the general shape of a gun, a light applicator comprising a light guide, an connection means comprising the components of a bayonet connection.

As shown in FIG. 6, the light applicator 38 may also comprise a light guide. As in the previous embodiments, the light applicator 38 is configured in size and shape for being at least partially inserted into a patient's mouth during a dental procedure. This embodiment is particularly useful when the light source, not shown, is contained within the gripping member 28 or in another remote location. This embodiment is also useful for attaching a Denbur type attachment tip 72 to the light guide inasmuch as Denbur type attachments, such as the Lite-Tip® are specifically configured for being attached to a light guide.

The gripping member 28 in this embodiment comprises the general shape of a gun and is configured to interconnect with the light guide and to transmit light to the light guide for transmission to the desired application site. As in the previous embodiments, the gripping member 28 is also configured for being held within the hand of a dental practitioner. The handle of the gripping member 28 may include any conventional handle typically embodied within existing light-curing devices in the art. The controls 52 for operating the light-curing device may include a trigger, as shown, or they may comprise other configurations and combinations of control buttons.

The light-curing device 18 also includes connection means 48 for detachably connecting the gripping member 28 and the light applicator 38 in a manner configured for preventing significant rotation of the light applicator 38 with respect to the gripping member 28. In the present embodiment, the connection means 48 includes the components of a bayonet type connection. In particular, the connection means 48 includes a radial slot formation 48A configured to receivably engage a pin 48B. Once the pin 48B is appropriately inserted and radially disposed within the radial slot formation 48A, such that the pin 48B is disposed within the retaining portion 48C of the radial slot formation 48A, then the connection means 48 is effectively able to prevent significant rotation of the light applicator 38 with respect to the gripping member. This embodiment is also useful for preventing longitudinal displacement of the light applicator 38 with respect to the gripping member 28, as generally described above.

In summary, the light-curing devices of the invention are configured with connection means for detachably connecting the gripping member and the light applicator in a manner preventing significant rotation of the light applicator during use, while enabling the light applicator to be controllably detached from the gripping member between uses. It should be appreciated that these are improvements over the existing devices in the art.

One method for using the light-curing devices of the invention is to insert the portion of the light applicator that includes the transparent shield into the mouth of a patient and to compress the transparent shield against a dental surface, a light-sensitive compound, a matrix band, another dental device placed within the patient's mouth, or any combination of the above. The transparent shield can be compressed against the desired surfaces, compounds, and any other devices, for example, by applying a force to the gripping member of the light-curing device. The forces applied to the gripping member will be transferred through the interconnected light applicator to the transparent attachment and finally to the desired location. It will be appreciated that in this manner the user can manipulate the light-sensitive compounds and hold a matrix band in a secure position during the dental procedure.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A light-curing device comprising:
   a gripping member sized and configured to be held in the hand of a user;
   a light applicator sized and configured for insertion at least partially into a patient's mouth in order to direct light to a desired location within the patient's mouth;
   a light source at least partially disposed within the light applicator and configured to generate and emit light suitable for curing a light-curable compound;

connection means for detachably connecting the gripping member and the light applicator in a manner so as to prevent significant rotation of the light applicator relative to the gripping member and for preventing longitudinal displacement of the light applicator relative to the gripping member.

2. A light-curing device as recited in claim 1, wherein the light applicator includes a light guide.

3. A light-curing device as recited in claim 1, further including a light source configured to generate and emit light suitable for curing a light-curable compound.

4. A light-curing device as recited in claim 3, wherein the light source includes at least one LED or LED array.

5. A light-curing device as recited in claim 3, wherein the light source is at least partially disposed within the gripping member.

6. A light-curing device as recited in claim 3, wherein the light source is at least partially disposed within the light applicator, such that the light applicator includes the light source and mounting structure configured to support the light source.

7. A light-curing device as recited in claim 1, wherein significant rotation includes an angular rotation of the light applicator relative to the gripping member that is greater than 10°.

8. A light-curing device as recited in claim 1, wherein the connection means includes the components of a bayonet connection.

9. A light-curing device as recited in claim 1, wherein the connection means includes the components of a tongue and groove connection.

10. A light-curing device as recited in claim 1, wherein the connection means includes at least one pin and at least one corresponding pinhole.

11. A light-curing device as recited in claim 1, wherein the connection means includes the components of a latching connection.

12. A light-curing device as recited in claim 1, wherein the light applicator includes structure configured for manipulation of a light-curable compound.

13. A light-curing device as recited in claim 12, wherein the structure configured for manipulation of a light-curable compound comprises an attachment that includes a transparent tip through which light passes during light-curing.

14. A light curing device as recited in claim 1, wherein the light curing device includes at least one pin that is electrically conductive so as to electrically couple the light applicator and gripping member.

15. A light curing device as recited in claim 1, wherein the light applicator includes a lens that is able to focus light emitted by the light applicator in a desired manner.

16. A light curing device as recited in claim 15, wherein the lens is detachably connected to the light applicator.

17. A light-curing device comprising:
a gripping member sized and configured to be held in the hand of a user;
a light applicator sized and configured for insertion at least partially into a patient's mouth in order to direct light to a desired location within the patient's mouth;
a light source at least partially disposed within the light applicator and configured to generate and emit light suitable for outing a light-curable compound;
a transparent tip connected to an end of the light applicator so that light emitted by the light source passes through the transparent tip; and
interconnecting structure for connecting the gripping member and the light applicator in a manner so as to prevent significant rotation of the light applicator relative to the gripping member and for preventing longitudinal displacement of the light applicator relative to the gripping member.

18. A light-curing device as recited in claim 17, wherein the light source includes at least one LED or LED array.

19. A light-curing device as recited in claim 17, wherein the interconnecting structure includes the components of at least one of a bayonet connection, a tongue and groove connection, a pin and pinhole connection, and a latching connection.

20. A light-curing device as recited in claim 17, wherein the structure configured for manipulation of the light-curable compound includes a transparent tip.

21. A light curing device as recited in claim 17, wherein the interconnecting structure includes at least one pin that is electrically conductive so as to electrically couple the light applicator and gripping member and provide power to the light source during use.

22. A light curing device as recited in claim 17, wherein the transparent tip is detachably connected to the light applicator and comprises a lens that is able to focus light emitted by the light applicator in a desired manner.

23. A light-curing device comprising:
a gripping member sized and configured to be held in the hand of a user;
a light applicator sized and configured for insertion at least partially into a patient's mouth in order to direct light to a desired location within the patient's mouth, the light applicator including structure configured for manipulation of the light-curable compound;
a light source at least partially disposed within the light applicator and configured to generate and emit light suitable for curing a light-curable compound; and
interconnecting structure for connecting the gripping member and the light applicator in a manner so as to prevent significant rotation of the light applicator relative to the gripping member and for preventing longitudinal displacement of the light applicator relative to the gripping member during manipulation of the light-curable compound.

24. A light-curing device as recited in claim 23, wherein the interconnecting structure includes the components of at least one of a bayonet connection, a tongue and groove connection, a pin and pinhole connection, and a latch.

25. A light-curing device as recited in claim 23, wherein the structure configured for manipulation of the light-curable compound includes a transparent tip.

* * * * *

UNITED STATES PATENT AND TRADEMARK OFFICE
CERTIFICATE OF CORRECTION

PATENT NO. : 6,702,576 B2
DATED : March 9, 2004
INVENTOR(S) : Fischer et al.

It is certified that error appears in the above-identified patent and that said Letters Patent is hereby corrected as shown below:

Column 1,
Line 20, replace first instance of "to" with -- too --
Line 24, delete "desire" and replace with -- desired --

Column 3,
Lines 43 and 49, delete "an" and replace with -- a --

Colume 10,
Line 3, delete "outing" and replace with -- curing --

Signed and Sealed this

Seventh Day of September, 2004

JON W. DUDAS
*Director of the United States Patent and Trademark Office*